(12) United States Patent
Ohkura et al.

(10) Patent No.: US 8,224,062 B2
(45) Date of Patent: Jul. 17, 2012

(54) METHOD AND APPARATUS FOR INSPECTION OF WAFER AND SEMICONDUCTOR DEVICE

(75) Inventors: Yoshihiro Ohkura, Iwata (JP); Yoshio Fukuda, Ebino (JP)

(73) Assignee: Yamaha Corporation, Hamamatsu-Shi (JP)

( * ) Notice: Subject to any disclaimer, the term of this patent is extended or adjusted under 35 U.S.C. 154(b) by 977 days.

(21) Appl. No.: 11/837,261

(22) Filed: Aug. 10, 2007

(65) Prior Publication Data

US 2008/0037859 A1    Feb. 14, 2008

(30) Foreign Application Priority Data

Aug. 14, 2006   (JP) .................................. 2006-220898
Oct. 11, 2006   (JP) .................................. 2006-277490

(51) Int. Cl.
   *G06K 9/62*        (2006.01)
(52) U.S. Cl. ....................................................... 382/149
(58) Field of Classification Search ...................... None
   See application file for complete search history.

(56) References Cited

U.S. PATENT DOCUMENTS

| 5,334,844 | A  | * | 8/1994 | Pollard et al. ............... 250/330 |
| 6,339,337 | B1 |   | 1/2002 | Matsuda et al. |
| 7,649,236 | B2 | * | 1/2010 | Fujii et al. ................... 257/458 |
| 2007/0181809 | A1 | * | 8/2007 | Chou et al. ................... 250/330 |

FOREIGN PATENT DOCUMENTS

| JP | 58-130256 | 9/1983 |
| JP | 59135353 | 8/1984 |
| JP | 06-148144 | 5/1994 |
| JP | 08068619 | 3/1996 |
| JP | 08-220008 | 8/1996 |
| JP | 10083975 | 3/1998 |
| JP | 10-312979 | 11/1998 |
| JP | 2003-51518 | 2/2003 |
| JP | 2004087634 | 3/2004 |
| JP | 2004-212159 | 7/2004 |
| JP | 2005332982 | 12/2005 |
| TW | 475061 B | 2/2002 |
| TW | 516083 B | 1/2003 |
| TW | 200503444 | 1/2005 |
| WO | WO-2005/124422 A1 | 12/2005 |

OTHER PUBLICATIONS

Translation of Detailed Descripton section of JP 08-220008, Aug. 30, 1996, 7 pages total.*
Translation of Detailed Description of JP 10-312979, Nov. 24, 1998, 6 pages total.*
Chinese Office Action issued for corresponding CN Application No. 200710140934.5, mailing date Dec. 16, 2011.

* cited by examiner

*Primary Examiner* — Brian P Werner
(74) *Attorney, Agent, or Firm* — Dickstein Shapiro LLP

(57) ABSTRACT

An individually isolated wafer adapted to a semiconductor chip is subjected to inspection in which an infrared ray is irradiated onto the backside of the wafer whose surface is sealed with a resin layer such that the optical axis thereof perpendicularly or slantingly crosses the surface of the wafer, whereby an image clearly showing cracks formed in the wafer is produced based on the reflected ray. Before or after an exterior inspection process, a tape inspection process is performed by use of an image of the surface of a dicing tape, in which a plurality of semiconductor chips are once attached onto and then separated from, so as to detect at least one of a defective element, a crack mark, and a foreign mark with regard to the semiconductor chip subjected to inspection.

9 Claims, 14 Drawing Sheets

METHOD AND APPARATUS FOR INSPECTION OF WAFER AND SEMICONDUCTOR DEVICE

BACKGROUND OF THE INVENTION

1. Field of the Invention

The present invention relates to methods and apparatuses for inspection of wafers, in particular for detection of cracks formed in wafers during dicing. The present invention also relates to methods for inspection of cracks and defects formed in semiconductor devices during manufacturing.

This application claims priority on Japanese Patent Application No. 2006-220898 and Japanese Patent Application No. 2006-277490, the contents of which are incorporated herein by reference.

2. Description of the Related Art

Due to recent developments of electronic devices such as portable terminals in terms of multiple functions and highly sophisticated functions, it is strongly demanded that semiconductor chips for use in electronic devices be downsized and reduced in thickness and be capable of performing high-speed processing. To meet such demands, semiconductor chips encapsulated in housings such as WL-CSP (i.e., Wafer Level Chip Size Package) have attracted attention of engineers and manufacturers. A typical example of the WL-CSP, i.e., a WL-CSP 1, will be described with reference to FIGS. 10 and 11. An IC 3, a pad electrode 4, a re-wire 5 electrically connected to the IC 3 via the pad electrode 4, and an electrode terminal (e.g., a metal post) 6 are formed on a surface 2a of a wafer 2 having a disk-like shape composed of polycrystal silicon or monocrystal silicon. In addition, resin sealing (i.e., formation of a resin layer 7) for protecting the IC 3 from heat, light exposure, and physical impact is also performed on the surface 2a of the wafer 2. In a last stage of manufacturing, individual ICs are isolated from each other by way of dicing along dicing lines 8. Thus, it is possible to simultaneously produce a plurality of semiconductor chips 1, each of which has an isolated wafer portion (i.e., a substrate) 2 having a rectangular shape in plan view, by use of a single wafer 2 having a disk-like shape. This noticeably improves the manufacturing efficiency, and this makes it possible to realize noticeable downsizing of the semiconductor chip 1 whose size is substantially identical to the size of the IC 3 after packaging.

During the manufacturing of the semiconductor chip 1 encapsulated in the WL-CSP, or during the conventionally-known manufacturing in which a wafer having a disk-like shape is subjected to dicing in advance so as to produce semiconductor chips, cracks, which are elongated inside of the semiconductor chips 1 from the cut surfaces of the wafer 2, may occur due to cutting resistance of dicing. For this reason, individually isolated semiconductor chips (or individually isolated portions, i.e., substrates, of a wafer) are subjected to inspection to determine whether or not cracks occur, thus checking the quality of products.

Japanese Unexamined Patent Application Publication No. H06-148144 teaches an example of an inspection device, in which semiconductor chips (or individually isolated wafers) are subjected to inspection using an ultrasonic image device equipped with a water tank storing pure water and an ultrasonic probe disposed in pure water of the water tank. In this inspection device, a semiconductor chip (or an inspected subject) is partially soaked in pure water, in which the ultrasonic probe scans the lower portion of the semiconductor chip while transmitting and receiving ultrasonic waves via pure water, whereby the inside of the semiconductor is converted into a visual image based on received reflection signals. This makes it possible to perform nondestructive inspection to determine whether or not cracks occur in the inside of the semiconductor chip or wafer.

In the ultrasonic inspection using the ultrasonic image device, it is necessary to provide pure water which the semiconductor chip (or the individually isolated wafer) is partially immersed in; and it is necessary to use dry baking for removing water content adhered to it after inspection. That is, a complex and troublesome operation is necessary in the ultrasonic inspection. In addition, the ultrasonic inspection needs human power for the maintenance of the ultrasonic probe precipitated in pure water. Furthermore, due to the immersion of the semiconductor chip in pure water during inspection, the semiconductor chip suffers from secondary appearance defects such as staining due to water content adhered thereto.

In order to accurately detect cracks elongated in slanted directions it is necessary to reduce the scanning speed of the ultrasonic probe, or it is necessary to perform scanning on one spot plural times. This increases the inspection time. Since the semiconductor chip is partially immersed in pure water during inspection, it is very difficult to simultaneously perform inspection on the lower surface and side surfaces (or cut surfaces) of the individually isolated wafer. This also increases the inspection time.

Japanese Unexamined Patent Application Publication No. 2003-51518 teaches a manufacturing method of a semiconductor device, in which ICs and pad electrodes are formed on the surface of a wafer having a disk-like shape composed of polycrystal silicon or monocrystal silicon, then, an extension sheet (or a dicing tape) for use in dicing is adhered onto the backside of the wafer. In this state, a probe is used to inspect the electric characteristics of the semiconductor chips formed on the wafer so as to check the qualities of the semiconductor chips, wherein inspection results are recorded on the backside of the dicing tape at prescribed positions corresponding to the semiconductor chips. Thereafter, the wafer is subjected to cutting (or dicing) so as to isolate individual semiconductor chips, wherein the individual semiconductor chips are subjected to screening based on the inspection results when they are separated from the dicing tape.

During dicing, cracks may be formed in the backside of the semiconductor chip produced using the wafer, or the semiconductor chip may be partially defective. The aforementioned document simply teaches the inspection of electrical characteristics of semiconductor chips prior to dicing; but this is an insufficient way of inspection of semiconductor chips.

The other conventionally-known technology teaches the exterior inspection in which, after dicing, semiconductor chips are each separated from a dicing tape so as to capture backside images thereof, so that cracks and defects formed in the backsides of the semiconductor chips can be visually detected; however, this method cannot always detect fine cracks and fine defects. Before dicing, the backside of die wafer forming semiconductor chips is subjected to polishing using a grinder so that the semiconductor chips are each reduced in thickness, wherein polished marks remain on the backsides of the semiconductor chips, which make it very difficult to detect cracks by way of the exterior inspection.

SUMMARY OF THE INVENTION

It is an object of the present invention to provide a method and apparatus for inspection of a wafer, which can realize efficient and reliable detection of cracks occurring in an individually isolated wafer subjected to dicing.

It is another object of the present invention to provide a method for detection of fine cracks and fine defects formed in a semiconductor chip with case.

In a first aspect of the present invention, there is provided a wafer inspection method for inspecting an individually isolated wafer following dicing, in which infrared rays are irradiated onto the backside of the wafer whose surface is sealed with a resin layer such that the optical axis thereof crosses the surface of the wafer, then, an image is produced based on the reflected rays so as to detect cracks formed in the wafer. It is preferable that the optical ark of the infrared rays slantingly cross the surface of the wafer It is preferable that a plurality of infrared rays be simultaneously irradiated onto four sides of the wafer having a rectangular he in plan view.

A crack inspection apparatus for inspecting a wafer whose surface is sealed with a resin layer is constituted of an illumination unit for outputting infrared rays toward the wafer, and an image copying unit that receives the reflected rays of the infrared rays irradiated onto the wafer so as to produce an image. It is preferable that a plurality of infrared rays be simultaneously irradiated onto four sides of the wafer having a rectangular shape in plan view. It is preferable that the illumination unit further include an infrared polarization filter.

In the above, the infrared rays are irradiated onto the backside of the wafer that is individually isolated by way of dicing, wherein it is transmitted through the wafer in which reflected rays occur due to irregular reflection of the infrared rays at the interface of a crack formed in the wafer. An image is produced based on the reflected ray so as to detect the crack formed in the wafer. This is a very simple method compared with the conventionally-known technology using the ultrasonic image device, which needs pure water that should be removed after inspection and which causes exterior defects such as stains in the wafer during inspection. In addition, it is possible to accurately detect edges of cracks, which are slantingly elongated in the wafer, irrespective of lengths of cracks; and it is possible to reduce the overall inspection time of use wafer.

When the infrared rays are irradiated such that the optical axis thereof slantingly crosses the surface of the wafer, it is possible to produce an image clearly showing and emphasizing cracks formed in the wafer. This is because the infrared rays reaching the planar surface of the wafer are subjected to regular reflection, while the infrared rays reaching the crack are subjected to irregular reflection responsive to the shape of the interface of the crack. For this reason, when the infrared rays are perpendicularly irradiated onto the surface of the wafer, the reflected rays occur in a direction perpendicular to the surface of the wafer; hence, an image produced based on the reflected rays shows the crack together with the IC pattern formed in the surface.

When the infrared rays are slantingly irradiated onto the surface of the wafer, the image pickup unit does not receive the reflected rays occurring due to regular reflection on the surface of the wafer but receives the reflected rays occurring due to irregular reflection depending upon the shape of the crack; hence, an image produced based on the received reflected rays clearly shows the crack, which is emphasized in contrast in comparison with other portions of the wafer. This makes it possible to reliably and visually recognize the existence of cracks formed in the wafer.

When plural infrared rays are simultaneously irradiated onto the four sides of the wafer having a rectangular shape, it is possible to simultaneously detect cracks elongated into the inside of the wafer from its four sides. This realizes an efficient way of inspection of the wafer with a reduced inspection time. When the infrared polarization filter is installed in an illumination unit, it is possible to reliably avoid the interference between plural infrared rays that are irradiated onto the four sides of the wafer, and it is therefore possible to produce an image clearly showing cracks.

In a second aspect of the present invention, an inspection method is introduced to inspect a plurality of semiconductor chips having integrated circuits, which are formed on the surface of a wafer and are individually isolated by way of dicing and in which the backside of the wafer is attached onto an adhesive layer formed on the surface of a dicing tape, wherein a tape inspection process is performed by use of an image of Tie dicing tape from which the plurality of semiconductor chips are separated and which shows at least one of a defective element of the semiconductor chip adhered onto the adhesive layer, a crack mark of the semiconductor chip formed on the surface of the dicing tape, and a foreign mark formed on the surface of the dicing tape. Herein, the defective element is detected from the semiconductor chip adhered onto the dicing tape. The crack mark is formed by a prescribed portion of the adhesive layer that is not adhered 1o a crack exposed on the backside of the semiconductor chip, wherein only the surrounding portion of the crack exposed in the backside of the semiconductor chip is still adhered to the adhesion layer, thus clearly showing the crack mark on the surface of the dicing tape. The foreign mark such as a wrinkle is formed by foreign matter such as dust, which is introduced between the dicing tape and mount stage or between the dicing tape and wafer. Due to the existence of the foreign matter, the dicing precision is degraded so that abnormalities such as defects and cracks occur on the side surfaces of semiconductor chips corresponding to the cut surfaces of the wafer.

Since the material of the dicing tape differs from the material of the defective element, it is possible to easily emphasize the contact between the defective element and the dicing tape in the Image of the dicing tape captured in the tape inspection process; this makes it possible to easily detect fine defects of semiconductor chips. In particular, it is possible to detect defects whose sizes are relatively small in view of the backsides of the semiconductor chips but are relatively large in view of the side surfaces of the semiconductor chips by way of the tape inspection process.

In the above, when at least one of the defective element, the crack mark, and the foreign mark is detected on the surface of the dicing tape on one side of a dicing line, both of the semiconductor chips attached to both sides of the dicing line are determined as defective products. In addition, before or after the tape inspection process, an exterior inspection process is performed by use of an image of the backside of the semiconductor chip, which is separated from the surface of the dicing tape so as to detect a defect or a crack exposed on the backside of the semiconductor chip. Alternatively, before the tape inspection process, an exterior inspection process is performed by use of an image of the backside of the semiconductor chip, which is separated from the surface of the dicing tape so as to detect a deflect or a crack exposed on the backside of the semiconductor chip, wherein the semiconductor chip in which neither the defect or crack is detected in the prior inspection process is subjected to the tape inspection process.

By performing both of the exterior inspection process end the tape inspection process, it is possible to reliably remove the "defective" semiconductor chips. When the exterior inspection process is performed before the tape inspection process in which the semiconductor chips including cracks and defects of relatively large sizes are determined in advance as defective products, it is possible to reduce the number of semiconductor chips subjected to the tape inspection process for inspecting fine defective elements, crack marks, and foreign marks; hence, it is possible to improve the inspection efficiency with regard to the semiconductor chips.

BRIEF DESCRIPTION OF THE DRAWINGS

These and other objects, sects, and embodiments of the present invention will be described in more detail with reference to the following drawings, in which.

DESCRIPTION OF THE PREFERRED EMBODIMENTS

Figure 1:
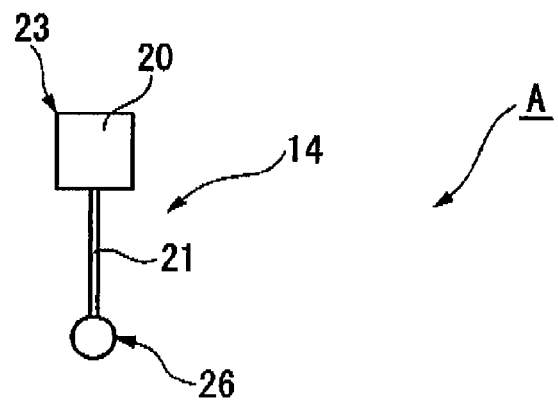
FIG. 1 is a plan view showing he overall constitution of a crack inspection apparatus adapted to a wafer in accordance with a first embodiment of the present invention.
Figure 1:
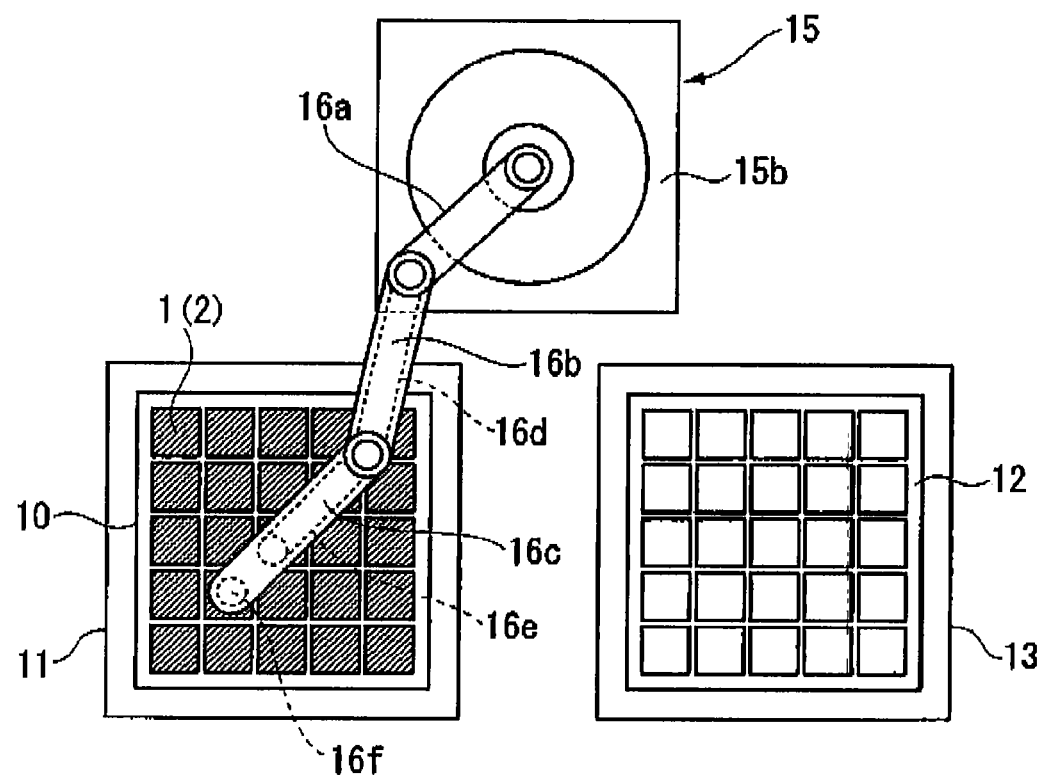

The present invention will be described in further detail by way of examples with reference to the accompanying drawings.

1. First Embodiment

A method and apparatus for Inspection of a wafer, specifically, for detection of cracks occurring in an individually isolated wafer subjected to dicing, according to a first embodiment of the present invention will be described with reference to FIGS. 1 to 7.

Specifically, the first embodiment is directed to an inspection method of a wafer 2 forming a semiconductor chip 1 encapsulated in a wafer level chip size package (WL-CSP) and a crack inspection apparatus A of the wafer 2. Herein, an IC 3, a pad electrode 4, a re-wire 5 electrically connected to the IC 3 via the pad electrode 4, and an electrode terminal (i.e., a metal post) 6 are formed on a surface 2a of the wafer having a disk-like shape, which is composed of polycrystal silicon or monocrystal silicon, wherein resin sealing (i.e., formation of a resin layer 7) for protecting the IC 3 from heat, light exposure, and physical impact, and wherein in the last stage of manufacturing, the wafer 2 is subjected to dicing along dicing lines 8 so as to produce individually isolate semiconductor chips (or WL-CSP) 1. Incidentally, the first embodiment is not necessarily limited to the inspection of the WL-CSP 1 but is applicable to the inspection of the semiconductor chip 1, in which the IC 3, the re-wire 5, and the resin layer 6 are formed on an individually isolated portion of the wafer 2 subjected to dicing.

Next, the crack inspection apparatus A adapted to the wafer 2 will be described with reference to FIGS. 1 and 2. The crack inspection apparatus A is constituted of a first mount stage 11 for mounting a first chip tray 10 storing a plurality of semiconductor chips 1 before inspection, a second mount stage 13 for mounting a second chip tray 12 storing the semiconductor chips 1 after inspection, an image capturing section 14 for producing an image by way of irradiation of infrared rays on the individually isolated wafer 2 of the semiconductor chip 1 and reception of reflected light, and a transport section 15 for transporting the first chip tray 10 storing the semiconductor chips 1 before inspection toward an inspection position and for storing the semiconductor chips 1 after inspection in the second chip tray 13. The image capturing section 14 is positioned opposite to the fist mount stage 11 and the second mount stage 13 by way of the transport section 15.

Figure 2:
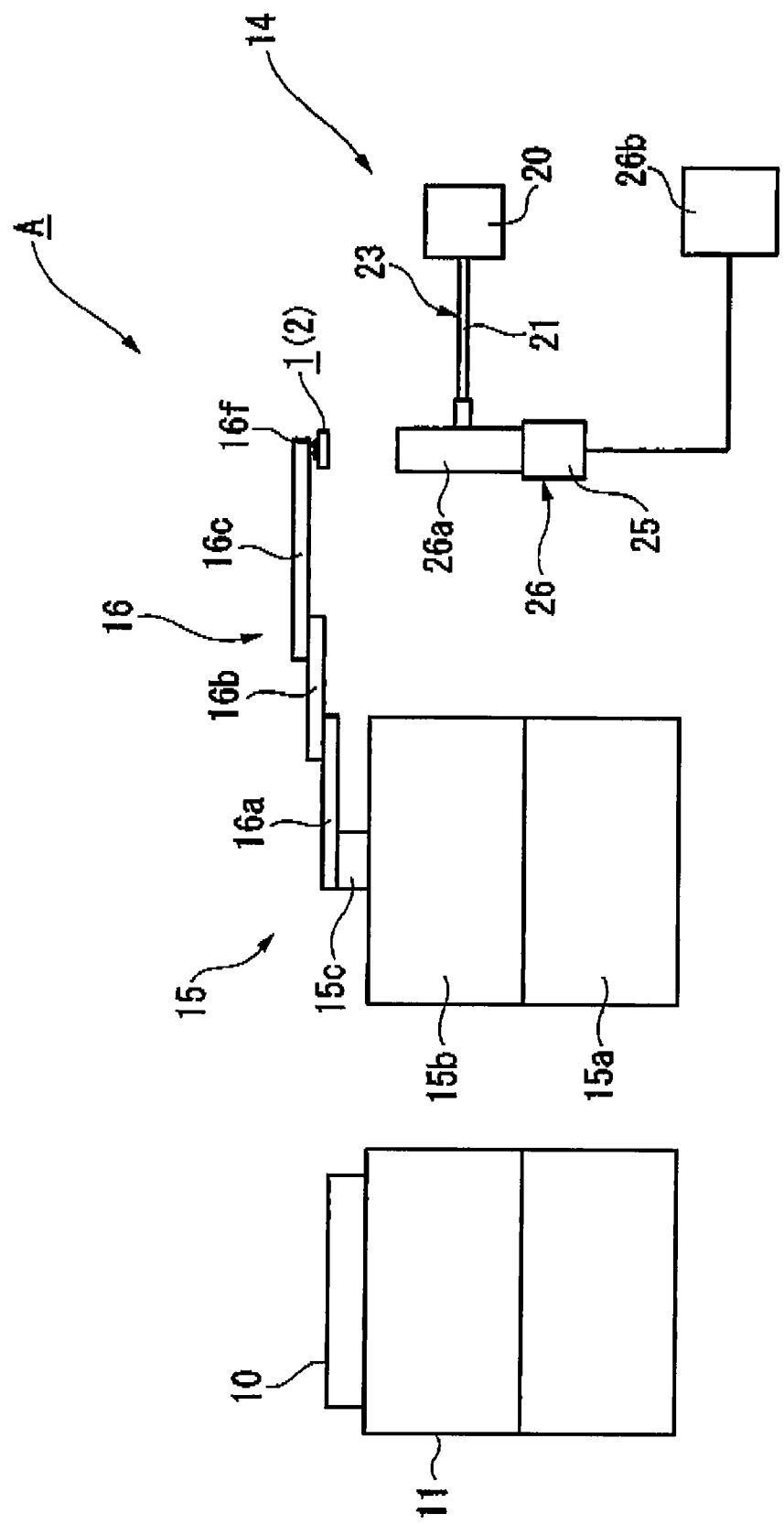
FIG. 2 is a side view diagrammatically showing the crack inspection apparatus including a first mount stage for mounting a first chip tray including a plurality of semiconductor chips, an image capturing section, and a transport section.
Figure 3:
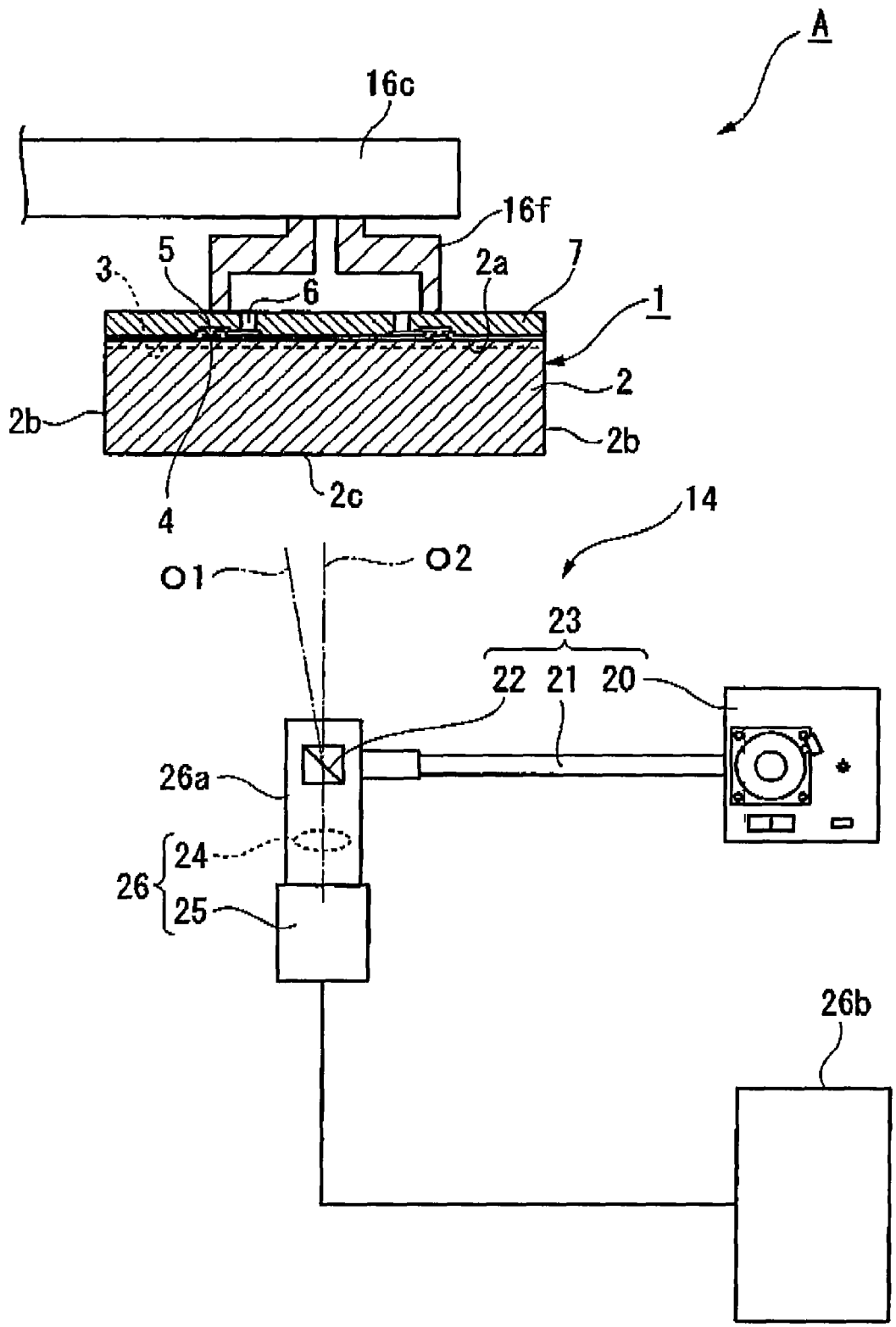
FIG. 3 is an enlarged side view showing an illumination unit and an image capturing unit included in the image capturing section together with a semiconductor chip held by a collet of a multiple-articulation arm included in the transport section.
Figure 4:
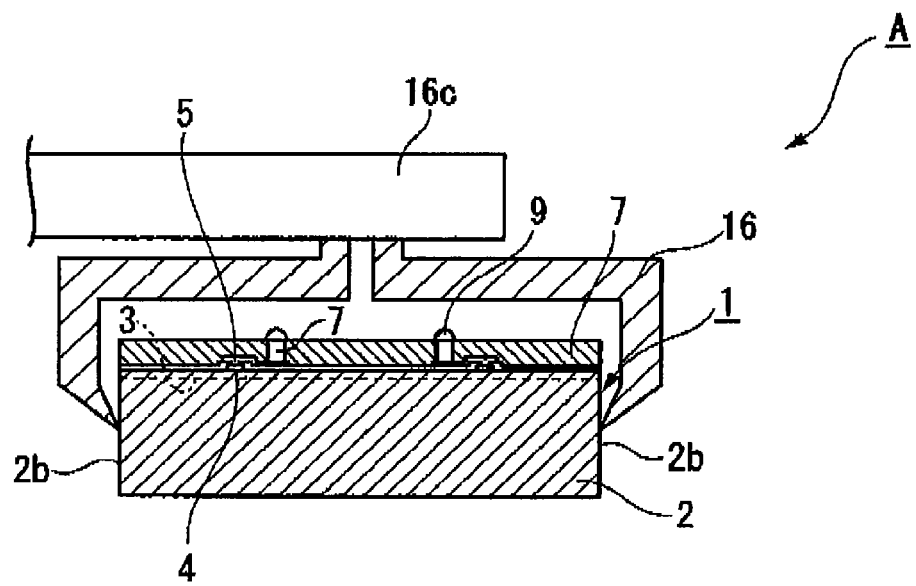
FIG. 4 is a side view party in cross section showing a variation of the collet of the transport section together with e image capturing section.
Figure 4:
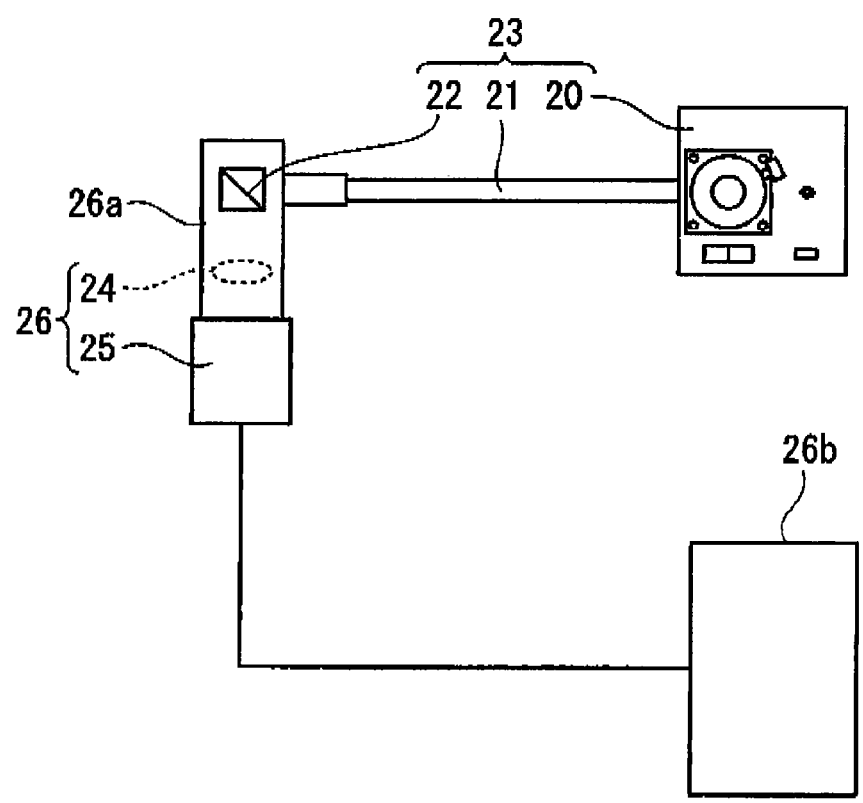

As shown in FIGS. 1 to 3, the transport section 15 is constituted of an XY table 15a, a rotary actuator 15b mounted on the XY table 15a in a vertical direction, and a multiple-articulation arm 16 connected to the upper end of a rotation shaft 15c of the rotary actuator 15b. The multiple-articulation arm 16 is constituted of a first arm 16a, a second arm 16b, and a third arm 16c, au of which are arranged in parallel with each other in a horizontal direction. A first end of the first arm 15a is connected to the upper end of the rotation shaft 15c so that the first arm 15a moves to follow the rotation of the rotation shaft 15c. A first end of the second arm 16b is axially supported in a rotatable manner by a second end of the first arm 16a, wherein the second arm 16b is rotatable about the second end of the first arm 16a by means of a belt transmission device 16d incorporated therein. A first end of the third arm 16c is axially supported in a rotatable manner by a second end of the second arm 16b, wherein the third arm 16c is rotatable about the second end of the second arm 16b by means of a belt transmission device 16e incorporated therein. A collet 16f projects downwardly from a second end of the third arm 16c and is absorbed to the upper surface of the semiconductor chip 1 so as to hold the semiconductor chip 1. A vacuum absorption device (not shown) is arranged inside of the collet 16f of the third arm 16c, wherein by driving the vacuum absorption device, the upper surface of the semiconductor chip 1 is absorbed to an opening of the collet 16f so that the semiconductor chip 1 is reliably held by the collet 16*f*. When bumps 9 are formed in the semiconductor chip 1 as shown in FIG. 4, the collet 16*f* is shaped to tightly hold the side surfaces of the semiconductor chip 1 (corresponding to cut surfaces 2*b* of the wafer 2).

As shown in FIGS. 1 to 3, the image capturing section 14 is arranged below the semiconductor chip 1, which is transported at a prescribed position by means of the transport section 15, so as to irradiate infrared rays to the back side of the semiconductor chip 1 (corresponding to a backside 2*c* of the wafer 2), wherein it is constituted of an illumination unit 23 and an IR camera (i.e., an infrared camera or an image capturing unit) 26. Specifically, the illumination unit 23 includes an IR source (i.e., an infrared source or a light source) 20 capable of outputting infrared rays whose wavelength is 1100 nm, for example, a fiberoptic bundle 21 for limiting an optical path of infrared rays output from the IR source 20, and a reflection mirror 22 for changing the direction of infrared rays output from the distal end of the fiberoptic bundle 21; and the illumination unit 26 includes a lens 24 and an image capturing element 25.

The IR source 20 of the illumination unit 23 is stored inside of a housing having a rectangular box shape. One end of the fiberoptic bundle 21 is arranged inside of the housing, while the distal end of the fiberoptic bundle 21 is extended in proximity to the reflection mirror 22 arranged inside of the IR camera 26. That is, one end of the fiberoptic bundle 21 receives infrared rays output from the IR source 20, wherein the received infrared rays are output toward the reflection mirror via the distal end of the fiberoptic bundle 21. The reflection mirror 22 is arranged inside of a housing 26*a* of the IR camera 26 and is set up in position so as to change the direction of the infrared rays, which are output from the distal end of the fiberoptic bundle 21 and are then irradiated to the wafer 2 positioned thereabove in such a way that an optical axis O1 of the infrared rays slantingly crosses the surface 2*a* of the wafer 2. The reflection mirror 22 is a half mirror connected to a controller (not shown) for changing the angle of the reflection mirror 22. This makes it possible to freely change the direction of the optical axis O1 of the infrared rays.

The IR camera 26 is installed in the housing 26*a* having a cylindrical shape, for example, wherein it is equipped with the lens 24 and the image capturing element 25 positioned below the lens 24. A wire connected to the image capturing element 25 is extended externally of the lower end of the housing 26*a* and is connected to a display 26*b* such as a monitor. The reflection mirror 22 is arranged above the lens 24 in such a way that the optical axis O1 of the infrared rays whose direction is changed by the reflection mirror 22 crosses an optical axis O2 of an optical system of the IR camera 26.

Next, a method for detection of cracks S occurring in the wafer 2 by use of the crack inspection apparatus A will be described with reference to FIGS. 1 to 3 and FIGS. 5 to 7.

First, the first chip tray 10 storing a plurality of semiconductor chips 1 is mounted on the first mount stage 11, and the "vacant" second chip tray 12 is mounted on the second mount stage 13. Next, the transport section 15 is driven so that the collet 16*f* attached to the second end of the third arm 16*c* is moved onto the first chip tray 10 so as to hold each of the semiconductor chips 1 subjected to transportation. The held semiconductor chips 1 are sequentially extracted from the first chip tray 10 and are then transported toward the image capturing section 14, wherein each of the semiconductor chips 1 is placed at a prescribed inspection position below which the reflection mirror 22 of the image capturing section 14 is positioned.

Next the IR source 20 of the image capturing section 14 irradiates infrared rays to the back side of the semiconductor chip 1, i.e., the backside 2*c* of the wafer 2. The infrared rays are transmitted through the fiberoptic bundle 21 and are then output from its second end toward the reflection mirror 22. Then, the reflection minor 22 changes the direction in such a way that the optical axis O1 of the infrared rays slantingly crosses the surface 2*a* of the wafer 2, so that the infrared rays are correspondingly irradiated to the backside 2*c* of the wafer 2.

Figure 5:
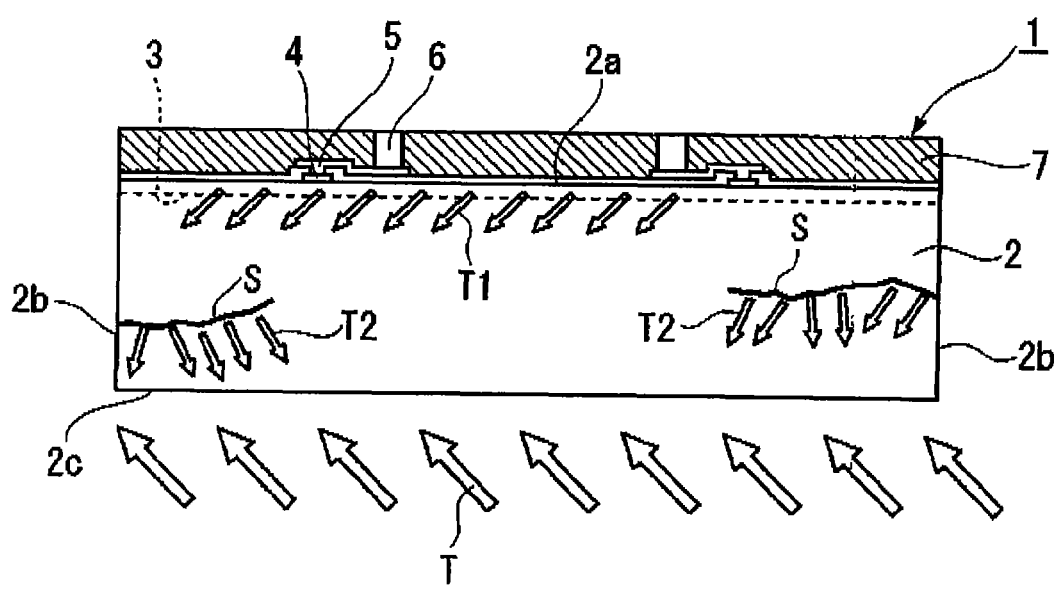
FIG. 5 is a cross-sectional view showing the semiconductor chip, in which to crack inspection apparatus irradiates infrared rays to the wafer.

Specifically, as shown in FIG. 5, infrared rays T, each having a prescribed wavelength of 1110 nm and each irradiated to the backside 2*c* of the wafer 2 are transmitted through the wafer 2. The transmitted infrared rays T have a relatively small ratio of absorption, in which they are absorbed by the resin layer 7 in a prescribed wavelength range, and a relatively small ratio of transmission, in which they are transmitted through the resin layer 7; hence, many of then are reflected on a joint interface between the rosin layer 7 and the source 2*a* of the wafer 2. At this time, the infrared rays T are each irradiated onto the surface 2*a* of the wafer 2 in such a way that the optical axis O1 thereof slantingly crosses the surface 2*a* of the wafer 2; hence, reflection rays T1 of the infrared rays T reaching the surface 2*a* are subjected to regular reflection on the surface 2*a*. Thus, even when the reflection rays T1 subjected to regular reflection are transmitted through the wafer 2 again and are then output toward the exterior of the wafer 2, they depart from the optical conversion range of the lens 24 of the IR camera 26, so that they are not subjected to imaging by means of the image capturing element 25.

Figure 6:
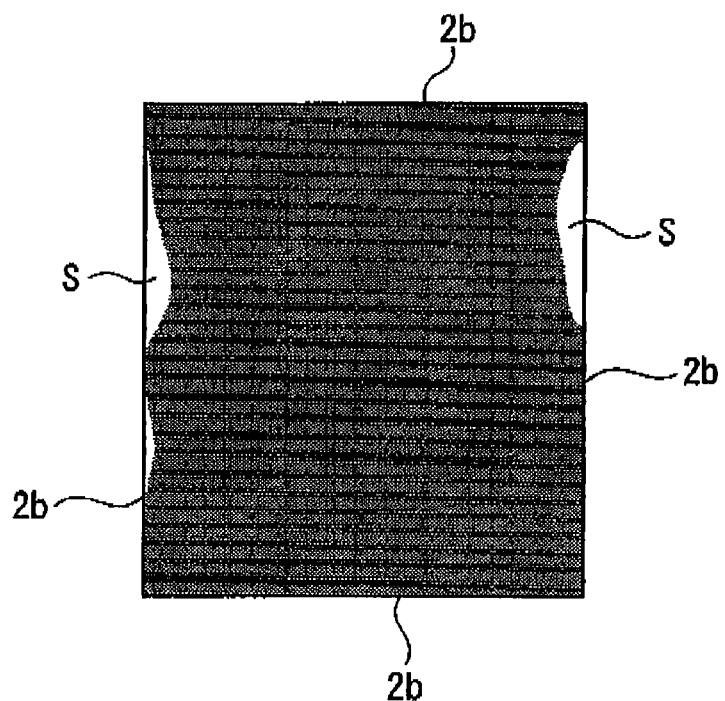
FIG. 6 shows an image that is from the wafer by means of the crack inspection apparatus.

When cracks S awe formed in the wafer 2 and are elongated inwardly from the cut surfaces (or side surfaces) 2*b* of the wafer 2 due to the cutting resistance during the dicing for individually isolating each of the semiconductor chips 1, the infrared rays T transmitted through the wafer 2 are subjected to scattering or irregular reflection in directions suiting the shapes of interfaces of the cracks S. Irrespective of the infrared rays T1 subjected to regular reflection, some of the reflection rays T2 subjected to irregular reflection are transmitted through the half mirror, i.e., the reflection mirror 22, so that they are received byte lens 24 of the IR camera 26. Thus, the reflection rays T2 subjected to irregular reflection at the cracks S are converged at the lens 24, so that the image capturing element 25 correspondingly produces an image. FIG. 6 shows an example of the image captured by the image capturing element 25, in which a contrast is emphasized between irregularly reflected portions (which are irregularly reflected on the interfaces of the cracks S) and regularly reflected portions (which are subjected to regular reflection on the surface 2*a* of the wafer 2), whereby it is possible to clearly show the edges of the cracks S. By use of the image that is produced by way of a simple operation in which infrared rays are irradiated onto the semiconductor chip 1, it is possible for an operator to make a visual recognition as to whether or not the cracks S occur in the semiconductor chip 1; thus makes it possible to easily check the quality of a product. Even when the cracks S re slantingly formed in the semiconductor chip 1, an image is produced based on the reflection rays T2, which are subjected to irregular reflection on the cracks S when the infrared rays T are irradiated onto the semiconductor chip 1; this makes it possible to reliably produce the image clearly showing the edges of the cracks S.

Figure 7:
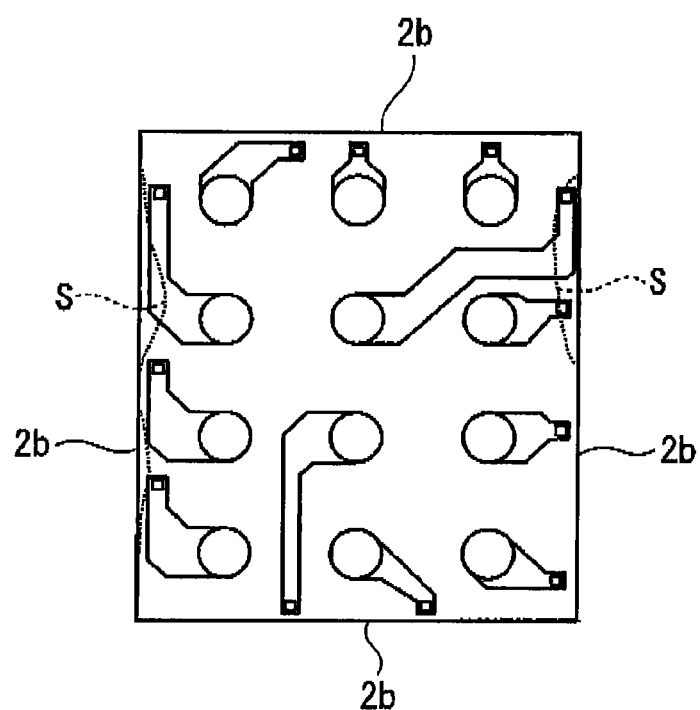
FIG. 7 shows an image that is produced by making the optical axis of the infrared ray perpendicularly cross the sure of the wafer.

When the infrared rays T are irradiated onto the surface 2*a* of the wafer 2 in such a way that the optical axis O1 thereof perpendicularly crosses the surface 2*a* of the wafer 2, the image capturing element 25 produces an image upon reception of the irregularly reflected portions of the reflection rays T2 subjected to irregular reflection on the interfaces of the cracks S and the regularly reflected portions of the reflection rays T2 subjected to regular reflection on the surface 2a of the wafer 2, wherein the image simultaneously shows the patterns of the ICs 3 formed on the surface 2a as well as shown in FIG. 7. This reduces distinctions of contrast between the cracks S and other portions of the semiconductor chip 1, whereby it becomes slightly difficult to distinguish the cracks S formed in the semiconductor chip 1.

After completion of the production of an image showing the cracks S formed in the wafer 2, the semiconductor chips 1 are each conveyed by the transport section 15 and are then stored in the second chip tray 12. At this time, it is possible to sort the semiconductor chips 1 in response to inspection results regarding the cracks S in such a way that the semiconductor chips 1 having the cracks S are returned to the first chip tray 10.

In the wafer inspection method and the crack inspection apparatus A according to the first embodiment, the infrared rays T are irradiated to the backside 2a of the wafer 2 so as to allow the infrared rays T to be transmitted through the wafer 2, wherein the infrared rays T are subjected to irregular reflection on the interfaces of the cracks 2 formed in the wafer 2. The image capturing element 25 produces an image upon reception of the reflection rays T2 subjected to irregular reflection, by which it is possible to perform inspection regarding the cracks S formed in the wafer 2. That is, with a simple operation in which the infrared rays T are irradiated onto the wafer 2 so as to produce an image based on the reflection rays T2, it is possible to reliably detect the cracks formed in the wafer 2. Compared with the foregoing inspection performed using the conventionally-known ultrasonic image device, the present embodiment has advantages in that it does not need pure water, it does not need to remove water content from the wafer 2 (or the semiconductor chip 1) after inspection and it avoids the occurrence of exterior defects such as strains of the wafer 2. By way of the inspection using infrared rays, the present embodiment is capable of accurately detecting the "slantingly formed" cracks 2; hence, it is possible to reduce the overall inspection time.

When the infrared rays T are irradiated onto the surface 2a of the wafer 2 in such a way that the optical axis O1 slantingly crosses the surface 2a, it is possible to produce a clear image having emphasized contrast between the cracks S and the other portions in the semiconductor chip 1. This makes it possible to produce a clear image emphasizing the cracks S based on only the reflection rays T2, which are subjected to irregular reflection in conformity with the shapes of the cracks S, without the reception of the reflected rays T1 subjected to regular reflection on the surface 2a.

The first embodiment is not necessarily limited to that described above and can be modified in a variety of ways. The first embodiment teaches that the crack inspection apparats A includes the image capturing section 14, the first mount stage 11, the second mount stage 13, and the transport section 15. Herein, the crack inspection apparatus A can be redesigned to include at least the image capturing section 14. The image capturing section 14 is not necessarily constituted of the illumination unit 20 (constituted of the IR source 20, the fiberoptic bundle 21, and the reflection mirror 22) and the image pickup unit 26 (constituted of the lens 24 and the image pickup element 25). That is, the image pickup section 14 can be redesigned such that the illumination unit 23 includes at least the IR source 20 for outputting the infrared rays T. In This case, it is necessary to provide a lens for receiving and converging the infrared rays T output from the IR source 20, whereby the infrared rays T are irradiated onto the wafer 2 via the lens.

In this respect, it is possible to provide another apparatus such as an exterior inspection apparatus (used for the manufacturing process of the semiconductor chips 1) with the image capturing section 14, whereby crack inspection is performed on the wafer 2 while performing exterior inspection by use of the existing transport section and chip tray mount stages equipped with the exterior inspection apparatus.

Figure 8:
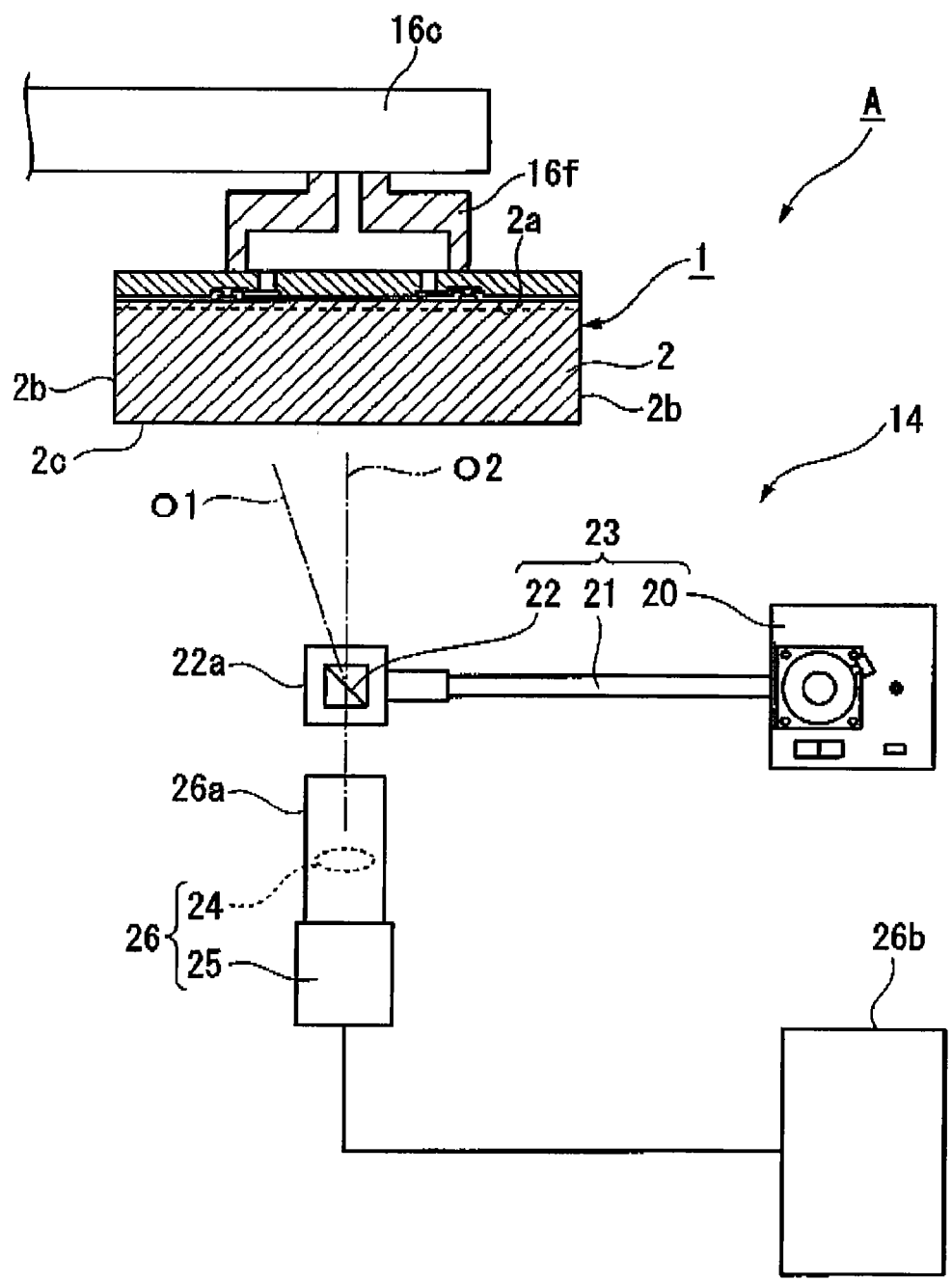
FIG. 8 is a side view partly in cross section showing the constitution of a crack inspection apparatus according to a variation of the first embodiment.

The present embodiment is designed such that the IR source 20 is stored in the rectangular-box-shaped housing of the illumination unit 23, and the lens 24 and the image capturing element 25 included in the image capturing unit 26 are stored in the cylindrically-shaped housing 26a, wherein the housings are not necessarily limited in the aforementioned shapes. The present embodiment is designed such that the reflection mirror 22 of the illumination unit 23 is arranged inside of the housing 26a of the image capturing unit 26, whereas it can be redesigned as shown in FIG. 8 in which the reflection mirror 22 is integrally formed with a box 22a connected to the second end of the fiberoptic bundle 21 of the illumination unit 23 so that the reflection mirror 22 is arranged independently of the image capturing unit 26. In this case, the optical axis O1 of the infrared ray T polarized by the reflection mirror 22 is varied by a control device (not shown) in such a way that it crosses the surface 2a of the wafer 2, wherein it is possible to detect cracks S by arranging the reflection mirror 22 between the image capturing unit 26 and the wafer 2. Incidentally, when the reflection mirror 22 is not arranged on the optical axis O2 of the optical system of the image capturing unit 26, it does not necessarily serve as a half mirror.

The present embodiment describes that the IR source 20 outputs the infrared ray T whose wavelength is 1100 nm or more. Of course, the wavelength is not necessarily limited to 1100 nm or more as long as the output beam of the IR source 20 belongs to the infrared range. The present embodiment describes that the wafer 2 is composed of polycrystal silicon or monocrystal silicon, whereas the wafer 2 is not necessarily composed of silicon material. The present embodiment can be easily modified to other types of wafers such as a wafer in which dicing tapes are adhered to the backside and a wafer which is held using dicing tapes after dicing, wherein the infrared rays output from the illumination unit 23 can be transmitted through dicing tapes so as to detect cracks.

Figure 9:
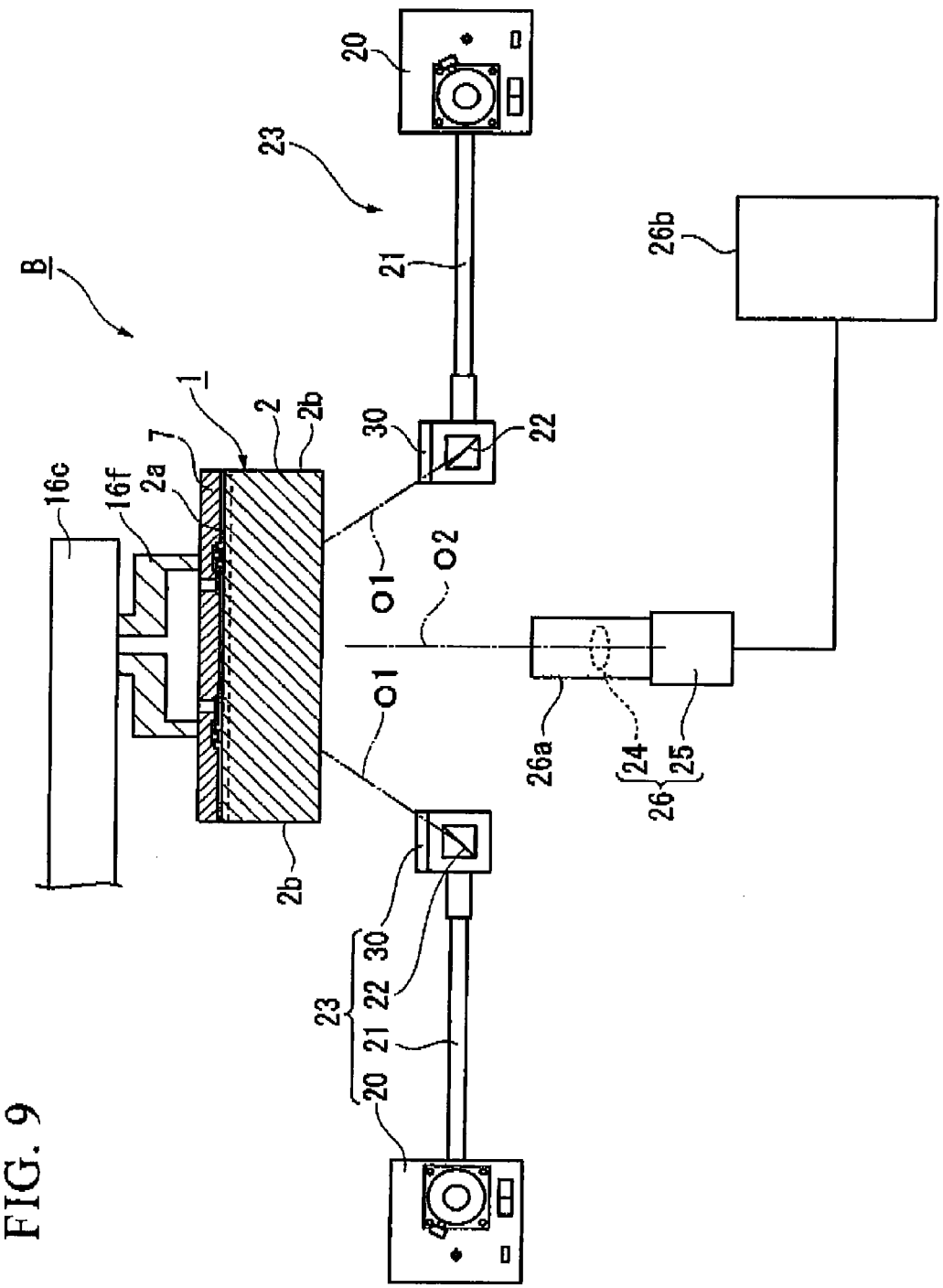
FIG. 9 is a side view party in cross section showing the constitution of a crack inspection apparatus in accordance with a second embodiment of the present invention.
Figure 10:
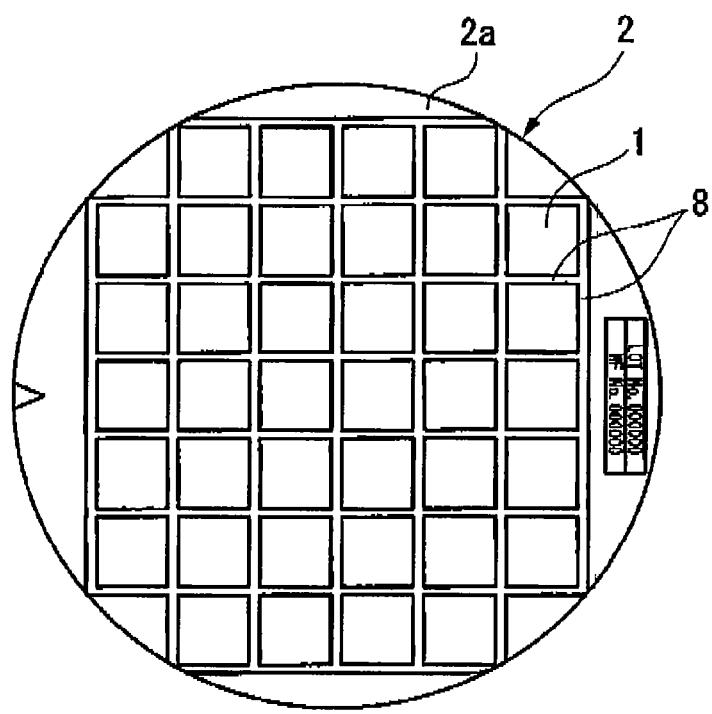
FIG. 10 is a plan view showing a wafer (realizing wafer level chip size packages) prior to dicing.
Figure 11:
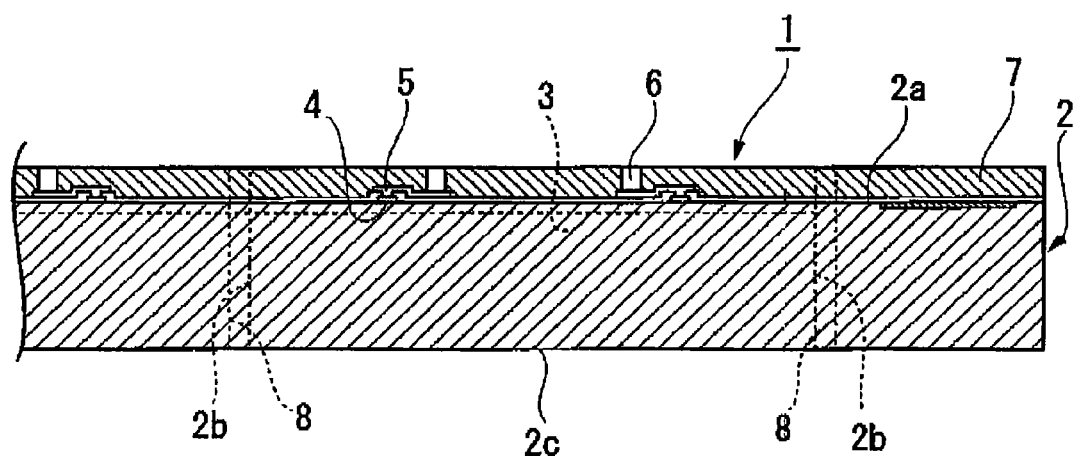
FIG. 11 is a cross-sectional view of the wafer.

Next, a variation of the first embodiment will be described with reference to FIG. 9, in which individually isolated wafers subjected to dicing are inspected so as to detect cracks. That is, a crack inspection apparatus B shown in FIG. 9 is basically similar to the crack inspection apparatus A shown in FIG. 3 except for the constitution of the image capturing section 14. In the crack inspection apparatus B, parts identical to those of the crack inspection apparatus A are designated by the same reference numerals; hence, the detailed description thereof will be omitted.

The image capturing section 14 is constituted of four illumination units 23 and one image capturing unit 26, wherein FIG. 9 simply shows two illumination units 23. Each illumination unit 23 is constituted of the IR source 20, the fiberoptic bundle 21, and the reflection mirror 22; and the image capturing it 26 is constituted of the lens 24 and the image capturing element 25.

The four illumination units 23 are respectively arranged along four sides of the semiconductor chip 1 having a rectangular Ape in plan view, i.e., along four side surfaces (or four cut surfaces) 2b of the wafer 2. Each illumination with 23 is adjusted to output the infrared rays T such that the optical axis O1 slantingly crosses the surface 2a of the wafer 2. That is, the four illumination units 23 are arranged such that the infrared rays T are irradiated into the inside of the semiconductor chip 1 from its four sides respectively. Each of the illumination units 23 includes an infrared polarization filter 30 for polarizing the infrared rays T output therefrom. By many of the infrared polarization filters 30, the infrared rays T output from the four illumination units 23 are adjusted so as not to interfere with each other. The image capturing unit 26 is arranged just below the semiconductor chip 1 in such a way that the optical axis O2 of the optical system thereof perpendicularly crosses the surface 2a of the wafer 2.

In the crack inspection apparatus B having the aforementioned constitution, the four illumination units 23 simultaneously irradiate the infrared rays T (as shown in FIG. 5) to the four side surfaces 2b of the wafer 2. Then, the reflected rays T2 due to irregular reflection at the cracks S formed in the wafer 2 are partially received by the image capturing unit 26 so as to produce an image clearly showing the cracks S. In the variation of the first embodiment, the infrared rays T are simultaneously irradiated to the four side surfaces 2b of the wafer 2 and are adjusted so as not to interfere with each other by means of the infrared polarization filters 30; hence, a single inspection allows the production of an image clearly showing the cracks that are elongated from the four side surfaces 2b to the inside of the wafer 2.

In the inspection method using the crack inspection apparatus B, the infrared rays T are simultaneously irradiated onto the four sides 2b of the wafer 2 having a rectangular shape in plan view so as to simultaneously detect the cracks that are elongated from the four side surfaces 2b to the inside of the wafer 2. This makes it possible to perform Inspection efficiently; hence, it is possible to reduce the overall inspection time. Herein, it is possible to avoid the interface between the infrared rays T irradiated onto the four sides 2b of the wafer 2 by means of the infrared polarization filters 30 installed in the illumination units 23; hence, it is possible to reliably produce an image clearly showing the cracks S.

The aforementioned variation of the first embodiment can be further modified within the scope of the invention. For example, the infrared polarization filters 30 are not necessarily installed in the illumination units 23. That is, when it is presumed that no interference occurs between the infrared rays T output from the illumination units 23, it is possible to omit the infrared polarization filters 30.

The aforementioned variation of the first embodiment is designed using the four illumination units 23, each of which is constituted of the IR source 20, the fiberoptic bundle 21, and the reflection mirror 22, wherein the infrared rays T are simultaneously irradiated onto the four sides 2b of the wafer 2; but this is not a restriction. It can be further modified in such a way that four fiberoptic bundles 21 are connected to a single IR source 20 so as to simultaneously irradiate the infrared rays T onto the four sides 2b of the wafer 2.

2. Second Embodiment

Figure 12:
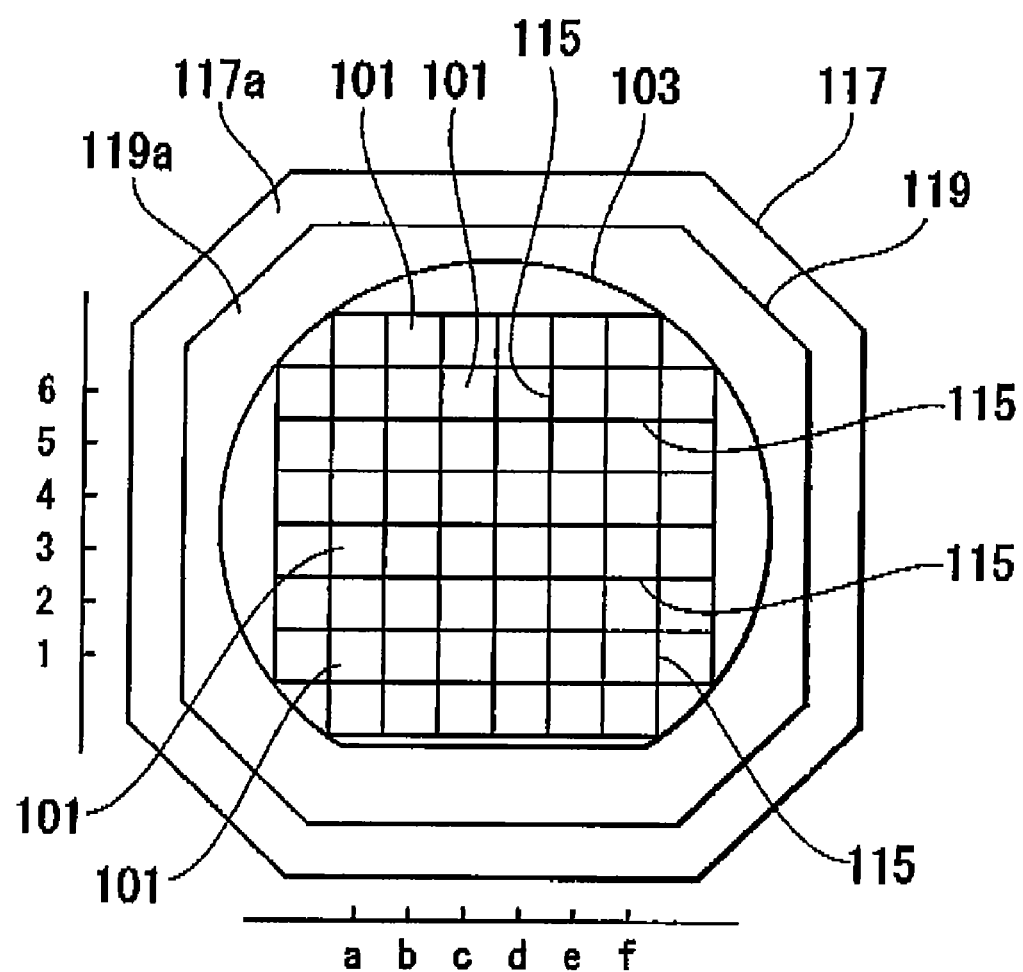
FIG. 12 is a plan view diagrammatically showing a plurality of semiconductor chips, which are subjected to inspection and are adhered onto a dicing tape.
Figure 13:
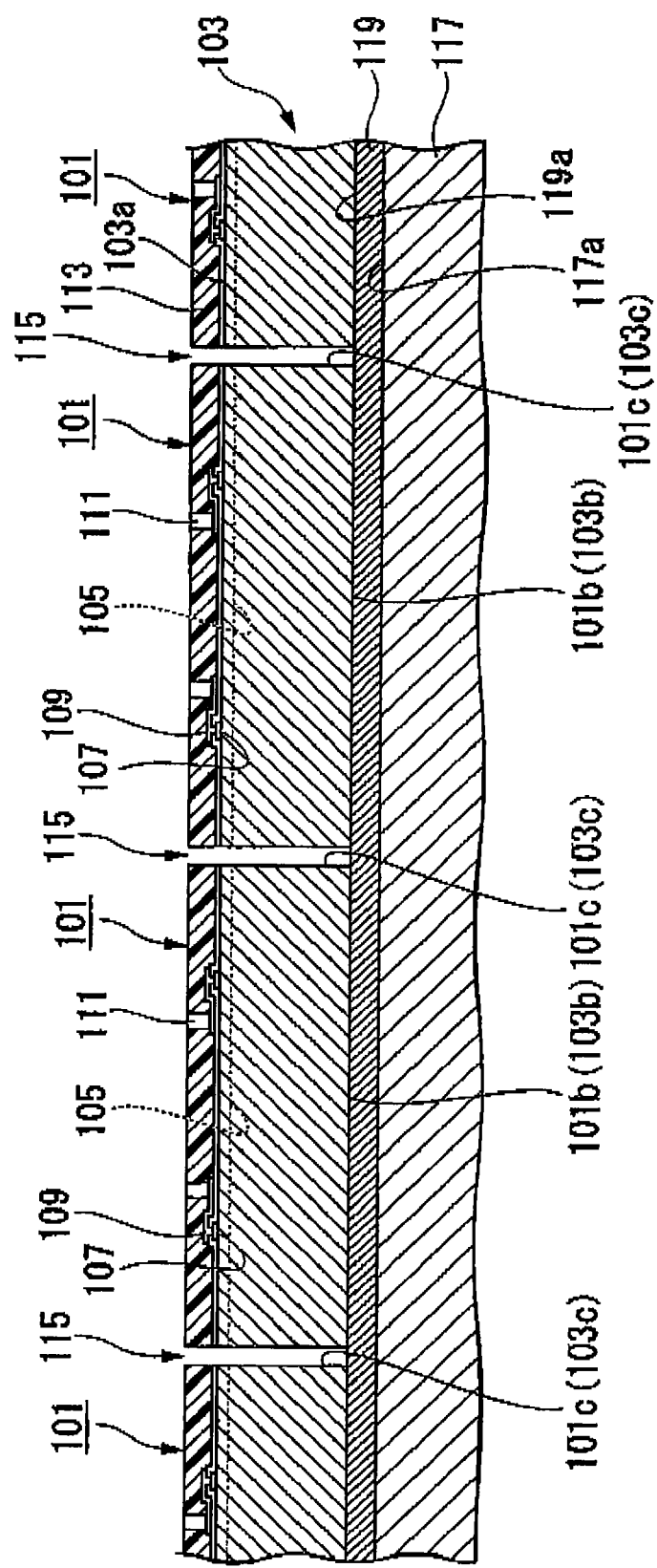
FIG. 13 is a cross-sectional view showing the constitution of the semiconductor chips, each of which is formed using a wafer and adhered onto the dicing tape.

An inspection method for semiconductor chips according to a second embodiment of the present invention will be described with reference to FIGS. 12 to 18. As shown in FIGS. 12 and 13, a plurality of semiconductor chips 101 subjected to inspection are produced by way of a wafer 103 having a disk-like shape composed of polycrystal silicon or monocrystal silicon.

A plurality of ICs 105, pad electrodes 107, re-wires 109 electrically connected to the ICs 5 via the pad electrodes 107, electrode terminals (or metal posts) 111, and resin layers 113 to protect the ICs 105 from heat, light radiation, and physical impacts are formed on a surface 103a of the wafer 103. Then, the wafer 103 is subjected to cutting (or dicing) using a thin grindstone having a disk-like shape along dicing lines (or cutting lines) on the surface 103a, thus individually isolating a plurality of semiconductor chips 101.

In the aforementioned dicing process, a dicing tape 119 (i.e., a stretchable and reducible sheet) is attached to a surface 117a of a mount stage 117, wherein a backside 103b of the wafer 103 opposite to the surface 103a is arranged just above a surface 119a of the dicing tape 119. An adhesive layer 121 (see FIGS. 16 and 17) having an adhesive property is formed on the surface 119a of the dicing tape 119; hence, the backside 103b of the wafer 103 is adhered to the surface 119a of the dicing tape 119.

The aforementioned semiconductor chip 101 is encapsulated in a wafer level chip size package (i.e., WL-CSP). Cut surfaces 103c of the wafer 103 adjoining dicing lines 115 form side surfaces 101c of the semiconductor chips 101; and the backside 103b of the wafer 103 forms backsides 101b of the semiconductor chips 101.

Figure 14:
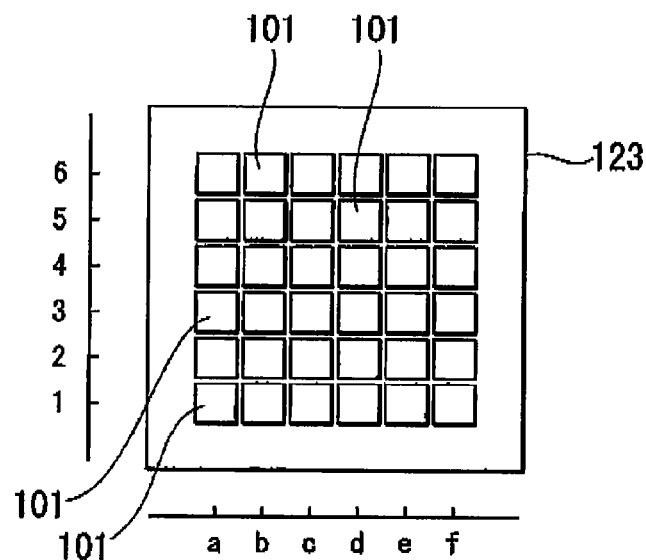
FIG. 14 is a plan view diagrammatically showing the semiconductor chips, which are separated from the dicing tape and are then transported onto a chip tray.

After completion of the dicing process, the semiconductor chips 101, which mutually adjoin each other, are slightly distanced from each other by stretching or expanding the dicing tape 119, wherein the semiconductor chips 101 are each separated from the diving tape 119 by means of a collet (not shown) and are then transported to a chip tray 123 shown in FIG. 14.

In the transport process as shown in FIGS. 12 and 14, within the plural semiconductor chips 101 individually isolated from each other, a prescribed number (e.g., twenty-four) of the semiconductor chips 101 positioned in the periphery of the wafer 103 are separated from the dicing tape 119 but are not transported to the chip tray 123, whereas the remaining (e.g., thirty-six) semiconductor chips 101 positioned in the effective area inwardly of the periphery of the wafer 103 are only transported to the chip tray 123.

Positional data of the semiconductor chips 101 of the effective area of the wafer 103, which are transported to the chip tray 123, are related to positional data recorded on the dicing tape 129 in correspondence with the semiconductor chips 101. The positional data of the semiconductor chips 101 are stored in a storage device of a personal computer (not shown), for example.

An inspection method of the present invention includes an electric characteristic inspection process, an exterior inspection process, and a tape inspection process with respect to the semiconductor chips 101 positioned in the effective area of the wafer 103.

In the electric characteristic inspection process, a probe (not shown) is used to inspect electric characteristics of the semiconductor chips 101 and to inspect electric conduction with respect to the ICs 105, the pad electrodes 107, the re-wires 109, and the electrode terminals 111. The electric characteristic inspection process is performed between the dicing process and the transport process. Inspection results are stored in the storage device in relation to the position data of the semiconductor chips 101.

The following exterior inspection process and the tape inspection process are not necessarily performed on the semiconductor chips 101 whose qualities are determined defective in the electric characteristic inspection process. This reduces the total number of the semiconductor chips 101 subjected to the exterior inspection process and the tape inspection process, thus improving the inspection efficiency. In the transport process, the semiconductor chips 101 whose qualities are determined to be defective in the electric characteristic inspection process are separated from the dicing tape 119 but are not necessarily transported to the chip tray 123. In other words, it is possible to transport only the semiconductor chips 101 whose qualities are determined good in the electric characteristic inspection process to the chip tray 123.

In the exterior inspection process, an image capturing device (not shown) captures an image of the backside 101b of the semiconductor chip 101, which is separated from the dicing tape 119 in the transport process, wherein based on the image, inspection is performed on a defect LP and a crack CP (see FIGS. 16 and 18) that are exposed on the backside 101b of the semiconductor chip 101. The defect LP and the crack CP are detected by detecting contrast visually observed in the image with respect to the defect LP and the crack CP exposed on the backside 101b of the semiconductor chip 101.

In the exterior inspection process, it is possible to detect a defective product corresponding to a semiconductor chip 101 in which at least one of the defect LP and the crack CP is detected in view of lie backside 101b. Inspection results are stored in the storage device in relation to the positional data of the semiconductor chips 101 on the dicing tape 119.

After completion of the exterior inspection process, it is possible to transport all the semiconductor chips 101 completed in the exterior inspection process to the chip tray 123. Alternatively, it is possible to transport only the good products corresponding to the semiconductor chips 101, in which neither the defect LP or crack CP is detected in the exterior inspection process, to the chip tray 123.

In the tape inspection process that is performed after completion of the transport process, the image capturing device (not shown) captures an image of the surface 119a of the dicing tape 19 so as to perform inspection of cracks or defects of to semiconductor chips 101 attached to the adhesive layer 121, crack marks of the semiconductor chips 101 formed in the adhesive layer 121, and foreign marks formed in the dicing tape 119.

The image of the surface 119a of the dicing tape 119 is produced in such a way that white light or laser beam is irradiated onto the surface 119a of the dicing tape 119, and then the reflected light is converged by the image capturing device so as to produce the image.

Figure 15:
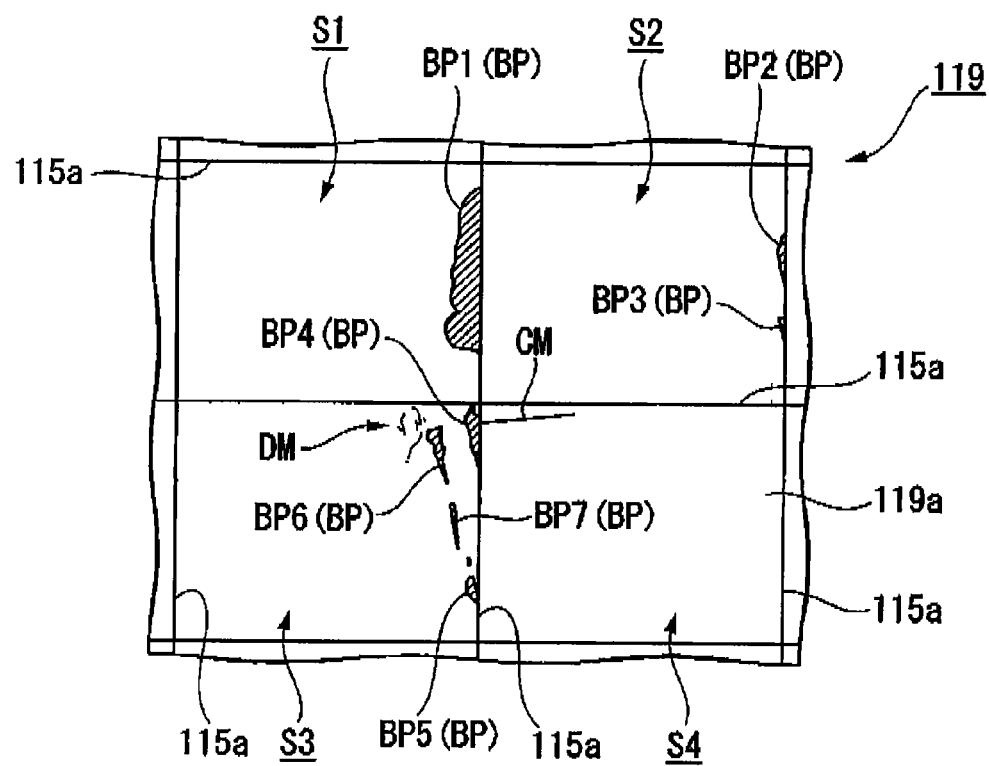
FIG. 15 shows an image showing the surface of the dicing tape from which the semiconductor chips are separated.

As shown in FIG. 15, the image of the surface 119a of the dicing tape 119 clearly shows imprints such as imprints 115a on the dicing lines 115 (hereinafter, referred to as dicing imprints 115a), defective elements BP, crack marks CM, and foreign marks DM. The image of FIG. 15 shows four adhesive areas S1 to S4, on which the semiconductor chips 101 are adhered, within a prescribed urea of the surface 119a encompassed by the dicing imprints 115a.

A defective element BP1 having a relatively large size is adhered onto the first adhesive area S1 (i.e., the upper-left region in FIG. 15) at a position adjacent to the dicing imprint 115a of the second adhesive area S2 (i.e., the upper-right region in FIG. 15). In addition, defective elements BP2 and BP3 each having a relatively small size are adhered onto the second adhesive area S2 at positions adjacent to the dicing imprint 115a; and defective elements BP4 and BP5 each having a relatively small size are adhered onto the third adhesive area S3 (i.e., the lower-left region in FIG. 15) at positions adjacent to the dicing imprint 115a of the fourth adhesive area S4 (i.e., the lower-right region in FIG. 15). Furthermore, defective elements BP6 and BP7 each having a relatively small size are adhered onto the third adhesive area S3 at positions not adjoining the dicing imprint 115a.

Figure 16:
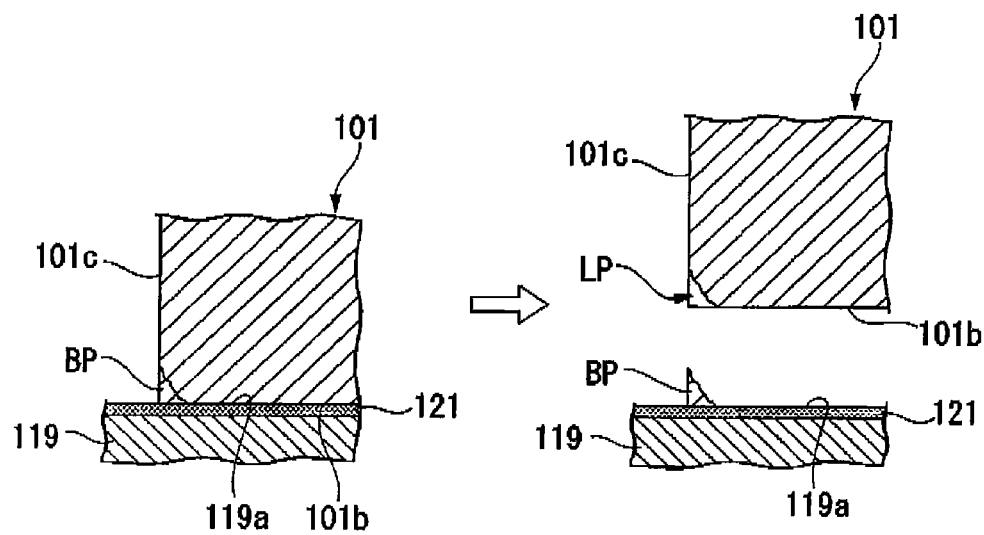
FIG. 16 includes cross-sectional views showing defective elements remaining on the surface of the dicing tape, from which the semiconductor chip is separated.
Figure 17:
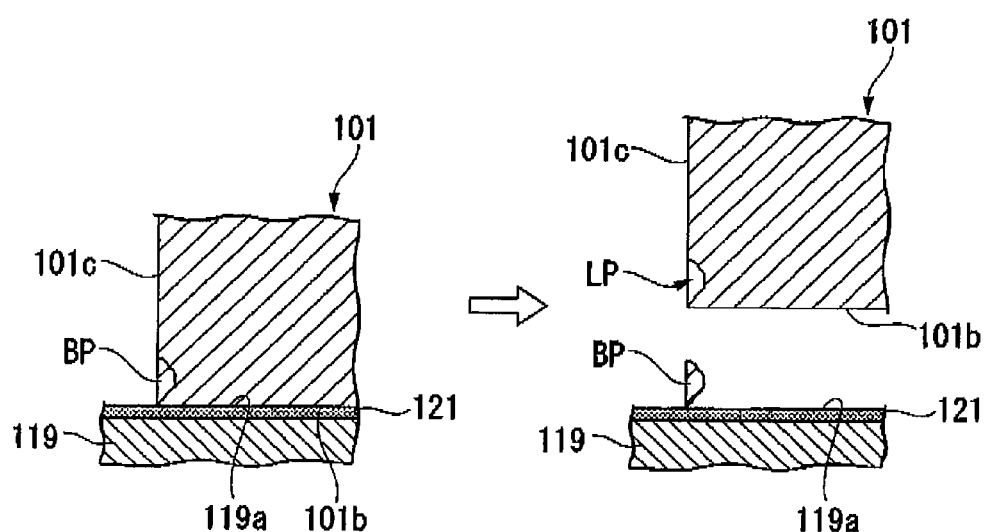
FIG. 17 includes cross-sectional views showing defective elements remaining on the surface of the dicing tape, from which the semiconductor- chip is separated.
Figure 18:
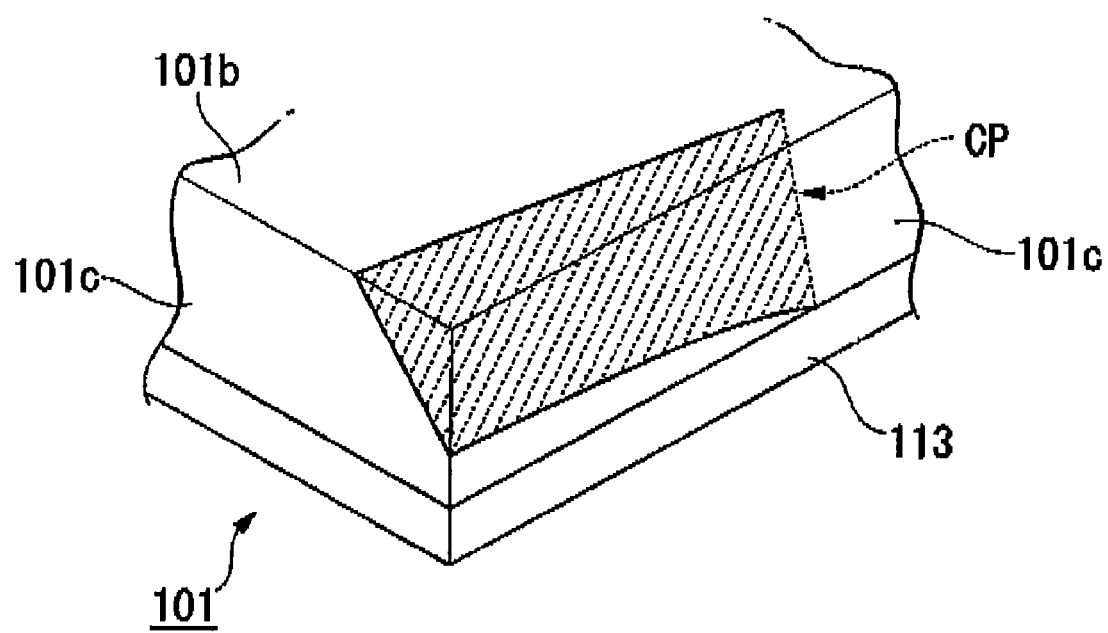
FIG. 18 is a perspective view showing the semiconductor chip adhered onto a prescribed area of the image shown in FIG. 15.

The defective elements BP are silicon defects remaining from the semiconductor chips 101, which are adhered onto the dicing tape 119 and are then separated from the dicing tape 119, wherein they each correspond to the defect LP of the semiconductor chip 101 shown in FIGS. 16 and 17.

Since the material of the dicing tape 119 differs tom the defective elements BP composed of silicon, it is possible to clearly detect the contrast between the defective elements BP and the dicing tape 119 in the image of FIG. 15. Specifically, the reflection ratio of the defective elements BP composed of silicon is higher than the reflection ratio of the surface 119a of the dicing tape 119; hence, the surface 119a of the dicing tape 119 is brighter than the defective elements BP in the image of FIG. 15. Therefore, even when a fine defective element BP remains on the surface 119a of the dicing tape 119 in correspondence with the defect LP of the semiconductor chip 101, it is possible to easily detect the fine defective element BP due to the contrast between the defective element BP and the dicing tape 119.

Various types of defective elements BP remain on the surface 119a of the dicing tape 119. For example, FIG. 16 shows that the defective element BP remains on the surface 119a of the dicing tape 119 in correspondence with the defect LP whose size is relatively large in view of the backside 101b and the side surface 101c of the semiconductor chip 101. FIG. 17 shows that the defective element BP remains on the surface 119a of the dicing tape 119 in correspondence with the defect LP whose size is relatively small in view of the backside 101b but is relatively large in view of the side surface 101c of the semiconductor chip 101.

It is easy to detect the defect LP of the semiconductor chip 101 and the defective element BP whose size is relatively large in view of the backside 101b of the semiconductor chip 101 shown in FIG. 16 by way of the exterior inspection process and the tape inspection process. In contrast, it is difficult to detect the defect LP of the semiconductor chip 101 and the defective element BP whose size is relatively small in view of the backside 101b of the semiconductor chip 101 shown in FIG. 17 by way of the exterior inspection process. However, it is easy to detect the defect LP and the defective element BP shown in FIG. 17 by way of the tape inspection process in which the contrast between the defective element BP and the dicing tape 119 cam be emphasized.

In FIG. 15, a thin linear crack mark CM is formed in the fourth adhesive area S4, wherein it is elongated from the dicing imprint 115a between the third adhesive area S3 and the fourth adhesive area S4, and the distal end thereof does not reach the other dicing imprint 115a but is stopped within the fourth adhesive area S4.

That is, the crack mark CM is a mark of a crack CP (see FIG. 18) and is formed by the adhesive layer 121, which is not adhered to the crack CP exposed on the backside 101b of the semiconductor chip 101. In other words, a prescribed portion of the backside 101b of the semiconductor chip 101 corresponding to the crack CP is not adhered onto the adhesive layer 121, but the surrounding portion of the crack CP is adhered onto the adhesive layer 121. This makes it possible for the crack mark CM to be shown on the surface 119a of the dicing tape 119 due to the adhesion of the semiconductor chip 101 on the adhesive layer 121.

In the above, the contrast between the prescribed portion of the adhesive layer 121 (corresponding to the crack mark CM) that is not adhered to the crack CP and the other portion of the adhesive layer 121 adhered onto the backside 101b of the semiconductor chip 101 is emphasized in comparison with the contrast between the backside 101b of the semiconductor chip 101 and the crack CP exposed on the backside 101b. Specifically, the reflection ratio of the prescribed portion of the adhesive layer 121 that is not adhered to the crack CP is higher than the reflection ratio of the other portion of the adhesive layer 121 adhered onto the backside 101b of the semiconductor chip 101; hence, in the image of FIG. 15, the crack mark CM is brighter than the surface 119a of the dicing tape 119 adhered onto the backside 101b of the semiconductor chip 101.

As described above, it is possible to easily detect the fine crack CP exposed on the backside 101b of the semiconductor chip 101 and the crack mark CM formed on the surface 119a of the dicing tape 119.

When the semiconductor chip 101 adhered onto the fourth adhesive area S4 is visually observed using a magnifying microscope as shown in FIG. 7, it is confirmed that the crack CF is exposed on the backside 101b in correspondence with the crack ark CM. Specifically, it is confirmed that the crack CP is elongated through the inside of the semiconductor chip 101 composed of silicon so as to reach the side surface 101c, and the crack CP exposed on the backside 101b is thinner than the crack CP exposed on the side surface 101c. That is, a first portion of the sack CP exposed on the backside 101b is smaller than a second portion of the crack CP exposed on the side surface 101c and is therefore very difficult to detect by way of the exterior inspection process.

The fine crack CP that is exposed on the backside 101b of the semiconductor chip 101 with a very small size may be formed when a crack, which is formed on the side surface 101c of the semiconductor chip 101 (corresponding to cut surface 103c of the wafer 103) in the dicing process, is elongated through the inside of the semiconductor chip 101 so as to reach the backside 101b. Hence, it is possible to easily detect the fine crack CP formed on the side surface 101c of the semiconductor chip 101 in the dicing process by way of the tape inspection process.

As shown in FIG. 15, the foreign mark DM is formed in the third adhesive area S3 at a position adjacent to the dicing imprint 115a of the first adhesive area S1.

The foreign imprint DM visually recognized in the image of FIG. 15 is a foreign imprint such as a wrinkle that is formed in the dicing tape 119 due to foreign matter such as dust, which is introduced between the dicing tape 119 and the mount stage 117 when the dicing tape 119 is mounted on the mount stage 117 in the dicing process or which is introduced between the dicing tape 119 and the wafer 103 when the wafer 103 is adhered onto the surface 119a of the dicing tape 119.

Due to the existence of the foreign matter, the dicing precision of the dicing process is degraded so that an abnormality such as a defect or crack may be formed on the cut surface 103c of the wafer 103 corresponding to the side surface 101c of the semiconductor chip 101. There is a low possibility that the aforementioned foreign mark is formed on the backside 101b of the semiconductor chip 101.

In the tape inspection process, light that is irradiated onto the surface 119a of the dicing tape 119 subjected to image capturing processing is subjected to irregular reflection at the foreign mark DM such as a wrinkle; hence, the foreign mark DM becomes brighter and clearer compared with the surface 119a of the dicing tape 119 in the image of FIG. 15.

For this reason, it is possible to easily detect the foreign mark DM by simply capturing an image of the dicing tape 119; hence, it is possible to easily detect the occurrence of an abnormality in the side surface 101c of the semiconductor chip 101.

In the tape inspection process, when at least one of the defective element BP, the crack mark CM, and the foreign mark DM is detected in the adhesive area of the dicing tape 119 adhering to the semiconductor chip 101 on the basis of the aforementioned image, the semiconductor chip 101 is determined to be a defective product. The semiconductor chip 101, which is determined to be a defective product, is removed from the chip tray 123 on the basis of the positional data of the semiconductor chip 101 on the dicing tape 119 and the positional data of the semiconductor chip 101 in to chip tray 123, both of which are stored in the storage device.

In the image of the dicing tape 119 shown in FIG. 15, each of the four adhesive areas S1 to S4 includes at least one of the defective elements BP, the crack mark CM, and the foreign mark DM; hence, all of the four semiconductor chips 101 respectively attached to the four adhesive areas S1 to S4 are detected as defective products.

The aforementioned tape inspection process can be performed with respect to all the semiconductor chips 101, which are completed in the exterior inspection process. Alternatively, the tape inspection process can be performed on only the semiconductor chips 101, which are determined as good products because neither defects or cracks are detected in the exterior inspection process.

In the aforementioned inspection method, the dicing tape 119 adhering a plurality of semiconductor chips 101 is simply subjected to image capturing processing after the dicing process; hence, it is possible to easily detect fine defects LP and fine cracks CP formed in the semiconductor chips 101. Since the foreign mark DM can be easily detected by simply rapturing an image of the dicing tape 119, it is possible to easily detect the occurrence of an abnormality on the side surface 101c of the semiconductor chip 101. In short, it is possible to accurately determine the quality of the semiconductor chip 101 based on the result of the tape inspection process.

The present embodiment inspects the semiconductor chips 101 by use of the dicing tape 119, which is conventionally used; this eliminates the necessity of using an additional inspection device; hence, this realizes low-cost inspection.

The present embodiment performs both of the exterior inspection process and the tape inspection process, thus reliably removing the "defective" semiconductor chips 101.

In particular, the exterior inspection process is performed before the tape inspection process, and the tape inspection process is performed on only the "good" semiconductor chips 101, in which neither defects LP or cracks CP are detected in the exterior inspection process. This reliably removes the "defective" semiconductor chips 101 having relatively large defects LP and relatively large cracks CP in advance by way of the exterior inspection process. This reduces the number of the semiconductor chips 101 subjected to the tape inspection process for detecting the fine defective elements BP as well as the crack mark CM and foreign mark DM; hence, it is possible to improve the inspection efficiency with respect to the semiconductor chips 101.

The present embodiment is designed such that light reflected on the spice 119a of the dicing tape 119 is subjected to convergence and image capturing processing so as to produce an image of the dicing tape 119 in the tape inspection process; but this is not a restriction. That is, the present embodiment simply requires to production of an image of the dicing tape 119 that distinguishes the defective elements BP, the crack mark CM, and the foreign mark DM.

For example, the dicing tape 119 is subjected to image capturing processing using a transparent film or a semitransparent film, wherein light is irradiated onto the surface 119a of the dicing tape 119, so that an image capturing device (not shown) performs convergence and image capturing processing on the light transmitted through the dicing tape 119. In this case, the light irradiated onto the surface 119a of the dicing tape 119 is reflected at the defective elements BP attached to the surface 119a of the dicing tape 119 and at the crack mark CM and the foreign mark DM formed on the surface 119a; hence, the image of the dicing tape 119 clearly shows the defective elements BP, the crack mark CM, and the foreign mark DM.

The present invention is not necessarily limited to the present embodiment in terms of the quality determination of the semiconductor chips 101 in the tape inspection process. For example, when at least one of the defective element BP, the crack mark CM, and the foreign mark DM is detected in a prescribed adhesive area of the surface 119a of the dicing tape 119 on one side of the dicing line 115 partitioning two semiconductor chips 101, it is possible to determine the two semiconductor chips 101 adhered on both sides of the dicing line 15 as defective products.

Suppose that the image of FIG. 15 does not clearly show the defective elements BP2 and BP3 attached to the second adhesive area 82. In this case, on the basis of the relatively large defective element BP1 attached to the first adhesive area S1 at a position adjoining the dicing imprint 115a with the second adhesive area S2, both semiconductor chips 101 respectively attached to the first adhesive area S1 and the second adhesive area S2 are determined to be defective products.

Suppose that the image of FIG. 15 does not clearly show the defective elements BP4 to BP7 and the foreign mark DM attached to the third adhesive area S3. In this case, on the basis of the crack mark CM that is formed in the fourth adhesive area S4 at a position adjoining the dicing imprint 115a with the third adhesive area S3, both of the two semiconductor chips 101 respectively attached to the third adhesive area S3 and the fourth adhesive area S4 are determined to be defective products.

Suppose that the image of FIG. 15 does not clearly show the defective element BP1 attached to the first adhesive area Si. In this case, on the basis of the foreign mark DM that is formed in the third adhesive area S3 at a position adjoining the dicing imprint 115a with the first adhesive area S1, both semiconductor chips 101 respectively attached to the first adhesive area S1 and the third adhesive area S3 are determined to be defective products.

The reason the qualities of the semiconductor chips 101 are determined as described above is that, when the defect LP and the clack CP are formed on the side surface 101c and the backside 101b of one semiconductor chip 101, which is attached to one side of the dicing line 115, abnormality such as the defect LP and the crack CP highly likely occurs in the side surface 101c of another semiconductor chip 101 adjoining the side surface 101c of one semiconductor chip 101. That is, by way of the aforementioned quality determination, it is possible to reliably remove the "defective" semiconductor chips 101.

The present embodiment describes such that the exterior inspection process is performed before the tape inspection process; but this is not a restriction. That is, the exterior inspection process can be performed after the tape inspection process. I this case, it is possible to reliably remove the "defective" semiconductor chips 101. Of course, it is possible to perform only the tape inspection process without performing the exterior inspection process.

In the present embodiment, the semiconductor chip 101 is constituted of the re-wire 109, the electrode terminal 111, and the resin layer 113 formed on the surface 103a of the wafer 103; but this is not a restriction. The present embodiment requires that at least the IC 105 and the pad electrode 107 be formed on the surface 103a of the wafer 103. In other words, the dicing process can be performed on the wafer 103 having the surface 103a on which the ICs 105 and the pad electrodes 107 are formed.

Lastly, the present invention is not necessarily limited to the aforementioned embodiments; hence, it can be farther modified in a variety of ways within the scope of the invention defined by the appended claims.

What is claimed is:

1. A wafer inspection method for inspecting an individually isolated wafer level chip size package following dicing, wherein the individually isolated wafer has a rectangular shape in plan view and top and bottom surfaces, and wherein the dicing creates four cut side surfaces on the individually isolated wafer, the wafer inspection method comprising:
   simultaneously irradiating a plurality of infrared rays onto the four cut side surfaces of the individually isolated wafer whose top surface is sealed with a resin layer such that an optical axis of the irradiated infrared rays is at an angle with respect to the top or bottom surface of the individually isolated wafer;
   receiving infrared rays reflected from an interface between the individually isolated wafer and the resin layer and infrared rays reflected from an interface of a crack, the reflected infrared rays being received by image capturing unit positioned below the individually isolated wafer, wherein an optical axis of the image capturing unit is perpendicular to the bottom surface of the individually isolated wafer; and
   producing an image based on the received reflected infrared rays so as to detect cracks formed in the individually isolated wafer.

2. A crack inspection apparatus for inspecting a wafer level chip size package that has a rectangular shape in plan view and top, bottom and four side surfaces, wherein the top surface is sealed with a resin layer, the apparatus comprising:
   an illumination unit for outputting a plurality of infrared rays simultaneously toward the four side surfaces of the wafer at an angle with respect to the top or bottom surface of the wafer level chip size package; and
   an image capturing unit that receives infrared rays reflected from an interface between the wafer level chip size package and the resin layer and infrared rays reflected from an interface of a crack, so as to produce an image, the image capturing unit being positioned below the wafer level chip size package, wherein an optical axis of the image capturing unit is perpendicular to the bottom surface of the wafer.

3. A crack inspection apparatus according to claim 2, wherein the illumination unit further includes an infrared polarization filter.

4. An inspection method for inspecting a plurality of semiconductor chips having integrated circuits, which are formed on a surface of a wafer and are individually isolated by way of dicing and in which a backside of the wafer is attached onto an adhesive layer formed on a surface of a dicing tape, wherein a tape inspection process is performed by use of an image of the dicing tape, from which the plurality of semiconductor chips are separated and which indicates at least one of a defective element of the semiconductor chip adhered onto the adhesive layer, a crack mark of the semiconductor chip formed on the surface of the dicing tape, and a foreign mark formed on the surface of the dicing tape.

5. An inspection method according to claim 4, wherein when at least one of the defective element, the crack mark, and the foreign mark is detected on the surface of the dicing tape on one side of a dicing line, both of the semiconductor chips attached to both sides of the dicing line are determined to be defective products.

6. An inspection method according to claim 4, wherein before or after the tape inspection process, an exterior inspection process is performed by use of an image of a backside of the semiconductor chip, which is separated from the surface of the dicing tape, thus detecting a defect or a crack exposed on the backside of the semiconductor chip.

7. An inspection method according to claim 5, wherein before or after the tape inspection process, an exterior inspection process is performed by use of an image of a backside of the semiconductor chip, which is separated from the surface of the dicing tape, thus detecting a defect or a crack exposed on the backside of the semiconductor chip.

8. An inspection method according to claim 4, wherein before the tape inspection process, an exterior inspection process is performed by use of an image of a backside of the semiconductor chip, which is separated from the surface of the dicing tape so as to detect a defect or a crack exposed on the backside of the semiconductor chip, and wherein the semiconductor chip in which neither the defect or the crack is detected in the exterior inspection process is subjected to the tape inspection process.

9. An inspection method according to claim 5, wherein before the tape inspection process, an exterior inspection process is performed by use of an image of a backside of the semiconductor chip, which is separated from the surface of the dicing tape so as to detect a defect or a crack exposed on the backside of the semiconductor chip, and wherein the semiconductor chip in which neither the defect or the crack is detected in the exterior inspection process is subjected to the tape inspection process.

* * * * *